(12) United States Patent
Raju et al.

(10) Patent No.: US 12,053,327 B2
(45) Date of Patent: Aug. 6, 2024

(54) DEVICES, SYSTEMS, AND METHODS FOR GUIDING REPEATED ULTRASOUND EXAMS FOR SERIAL MONITORING

(71) Applicant: KONINKLIJKE PHILIPS N.V., Eindhoven (NL)

(72) Inventors: Balasundar Iyyavu Raju, Cambridge, MA (US); Anthony M. Gades, Bothell, WA (US); Jing Ping Xu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 17/612,929

(22) PCT Filed: May 19, 2020

(86) PCT No.: PCT/EP2020/063884
§ 371 (c)(1),
(2) Date: Nov. 19, 2021

(87) PCT Pub. No.: WO2020/239518
PCT Pub. Date: Dec. 3, 2020

(65) Prior Publication Data
US 2022/0225966 A1 Jul. 21, 2022

(30) Foreign Application Priority Data
May 24, 2019 (WO) ................ PCT/CN2019/088303

(51) Int. Cl.
*A61B 8/08* (2006.01)
*A61B 8/00* (2006.01)
*G06T 7/00* (2017.01)

(52) U.S. Cl.
CPC ............ *A61B 8/5215* (2013.01); *A61B 8/465* (2013.01); *G06T 7/0012* (2013.01); *G06T 2207/10132* (2013.01)

(58) Field of Classification Search
None
See application file for complete search history.

(56) References Cited

U.S. PATENT DOCUMENTS

2008/0137927 A1 6/2008 Altmann et al.
2008/0181479 A1* 7/2008 Yang ........................ A61B 8/08
600/443

(Continued)

FOREIGN PATENT DOCUMENTS

WO 2018063811 A1 4/2018
WO 2019038210 A1 2/2019

OTHER PUBLICATIONS

International Search Report and Written Opinion for PCT/EP2020/063884, mailing date: Aug. 17, 2020, 8 pages.

(Continued)

*Primary Examiner* — Delomia L Gilliard

(57) ABSTRACT

Systems, devices, and methods are provided to provide serial monitoring for a patient. An ultrasound system is provided which may include subdividing a portion of the anatomy of a patient into a number of zones. Imaging data may be received by an imaging device. This imaging data may be used to generate a severity score for each zone based on imaging parameters within the imaging data. Changes in the severity score for each zone may be displayed over time, such that a medical professional may monitor each zone in a serial manner.

17 Claims, 6 Drawing Sheets

(56) References Cited

U.S. PATENT DOCUMENTS

2015/0310581 A1    10/2015  Radulescu et al.
2017/0086794 A1*   3/2017   Halmann ............. A61B 8/0875
2017/0091914 A1    3/2017   Halmann et al.
2017/0273668 A1    9/2017   Matsumoto

OTHER PUBLICATIONS

Doerschug et al., "Intensive Care Ultrasound: Ill Lung and Pleural Ultrasound for the Intensivist", Annals of the American Thoracic Society, Dec. 2013, vol. 10, No. 6, pp. 708-712.

Volpicelli et al., "International evidence-based recommendations for point-of-care lung ultrasound", Intensive Care Medicine, Apr. 2012, vol. 38, No. 4, pp. 577-591.

Chiem, Alan T. et al.,"Comparison of Expert and Novice Sonographers' Performance in Focused Lung Ultrasonography in Dyspnea (FLUID) to Diagnose Patients With Acute Heart Failure Syndrome", Acad Emerg Med, 2015, 22(5), pp. 564-573.

Öhman, Jonas et al., Focused echocardiography and lung ultrasound protocol for guiding treatment in acute heart failure:, ESC Heart Failure, 2018, 5, pp. 120-128.

* cited by examiner

DEVICES, SYSTEMS, AND METHODS FOR GUIDING REPEATED ULTRASOUND EXAMS FOR SERIAL MONITORING

CROSS-REFERENCE TO PRIOR APPLICATIONS

This application is the U.S. National Phase application under 35 U.S.C. § 371 of International Application No. PCT/EP2020/063884, filed on May 19, 2020, which claims the benefit of Chinese Patent Application No. PCT/CN2019/088303, filed on May 24, 2019. These applications are hereby incorporated by reference herein.

TECHNICAL FIELD

The present disclosure relates to providing serial medical monitoring of a patient, and in particular, to guiding repeated ultrasound examinations of a patient in one or more specific anatomical zones. This monitoring may include receiving imaging data representative of an anatomical zone from one or more external ultrasound transducers, generating a severity score associated with the imaging data, and comparing this severity score to other severity scores associated with the anatomical zone.

BACKGROUND

Non-invasive point of care ultrasound imaging devices are used to diagnose various diseases including cardiovascular diseases and diseases within the lungs. The devices may require scanning at several locations within the anatomy of a patient. For example, ultrasound transducers may be used to scan several locations within the heart or lungs of a patient to evaluate cardiovascular problems or pneumonia. In the case of heart failure, pulmonary edema may occur leading to reverberation features referred to as B-lines. Since the location of these B-lines in the chest may vary, a typical examination may include imaging several locations in both the right and left sides of the chest of the patient.

Another example is evaluation of consolidation within the lungs in the case of pneumonia. This may require ultrasound imaging of various locations within the lungs. In a medical setting such as an intensive care unit (ICU), the patient may need to be monitored continually in order to evaluate if conditions in the heart or lungs are improving. This may need to be done in response to medications or interventions.

Repeating a full monitoring procedure for all locations may be time consuming, especially in a critical care setting, such as an ICU. For example, if several patients need to be monitored with limited instruments, the time allotted to each patient may be limited. Existing methods for tracking and analyzing ultrasound imaging data are often manual and ineffective in allowing a physician to synthesize and assess the complete health of the patient over time.

SUMMARY

Systems, devices, and methods for performing ultrasound imaging are provided. The ultrasound imaging system may include an ultrasound probe with an ultrasound transducer array that is used to gather imaging data from an area of anatomy of the patient. In some embodiments, the area of anatomy is divided into a number of sections or zones. The imaging data for each zone may be analyzed and the sections may be assigned a severity level for a particular time based on one or more parameters of the imaging data for the section. The system may be used to monitor the severity level for each zone over time. For example, a medical professional may be able to select a particular zone and access the temporal history for the zone over time. This may assist medical professionals to serially monitor a patient over time and be particularly useful for patients with more than one doctor. The system may also be used to assess the severity of medical conditions within the various zones and highlight severe areas for further watch by a medical professional. This may allow medical professionals to focus on the important areas of anatomy and reduce evaluation burden, especially in critical care situations.

An ultrasound imaging system is provided, which may include: an ultrasound transducer array, wherein the ultrasound transducer array is arranged to obtain imaging data associated with an anatomy of a patient, wherein the anatomy of the patient is spatially arranged in a plurality of zones; and a processor circuit in communication with the ultrasound transducer array, wherein the processor circuit is arranged to receive a first set of imaging data obtained by the ultrasound transducer array, wherein the first set of imaging data is representative of at least one of the plurality of zones, wherein the processor circuit is arranged to determine, for the at least one of the plurality of zones, a first severity score associated with an anatomical parameter based on the first set of imaging data, wherein the processor circuit is arranged to receive a second set of imaging data obtained by the ultrasound transducer array, wherein the second set of imaging data is representative of the at least one of the plurality of zones, wherein the processor circuit is arranged to determine, for the at least one of the plurality of zones, a second severity score associated with the anatomical parameter based on the second set of imaging data, wherein the processor circuit is arranged to output, to a display device in communication with the processor, a visual representation of the plurality of zones including indications of the first severity score and the second severity score.

In some embodiments, the first set of imaging data is representative of a first zone at a first time, and the second set of imaging data is representative of a second zone at the first time. In other embodiments, the first set of imaging data is representative of a first zone at a first time, and the second set of imaging data is representative of the first zone at a different, second time. The visual representation may illustrate a change in severity score over time based on the first severity score and the second severity score. The visual representation may include a plot of the change in severity score over time. The visual representation may include a chronological representation of at least one of the first set of imaging data, the second set of imaging data, the first severity score, or the second severity score. The processor circuit may be further arranged to spatially correlate the first and second sets of imaging data to the plurality of zones.

In some embodiments, the visual representation of the plurality of zones includes selectable representations of the plurality of zones such that selection of a zone by a user displays the first and second sets of imaging data correlated to the selected zone. The ultrasound array may be arranged to obtain imaging data associated with a lung of the patient. The parameter may include at least one of a degree of consolidation, a measurement of fluid in the lungs, a degree of lung collapse, a B-line number, a measurement of air bronchogram, or a measurement of plural effusion. The ultrasound array may be arranged to obtain imaging data associated with the heart of the patient. The parameter may be one or more of a physical dimension of heart chamber, an ejection fraction, a degree of blockage of a blood vessel, or a volume measurement.

A method of conducting ultrasound imaging is also provided, including: receiving, with a processor circuit, a first set of imaging data representative of at least one of the plurality of zones, wherein the processor circuit is in communication with an ultrasound transducer array, wherein the ultrasound transducer array is arranged to obtain imaging data associated with an anatomy of a patient spatially arranged in a plurality of zones; determining, with the processor circuit, a first severity score associated with an anatomical parameter based on the first set of imaging data, wherein the first severity score is associated with at least one of the plurality of zones; receiving, with the processor circuit, a second set of imaging data representative of the at least one of the plurality of zones; determining, with the processor circuit, a second severity score associated with the anatomical parameter based on the second set of imaging data, wherein the second severity score is associated with the at least one of the plurality of zones; and outputting, to a display device in communication with the processor circuit, a visual representation of the plurality of zones including indications of the first severity score and the second severity score.

In some embodiments, the first set of imaging data is representative of a first zone at a first time, and the second set of imaging data is representative of a second zone at the first time. In other embodiments, the first set of imaging data is representative of a first zone at a first time, and the second set of imaging data is representative of the first zone at a different, second time. The visual representation may illustrate a change in severity score over time based on the first severity score and the second severity score. The visual representation may include a plot of the change in severity score over time. The visual representation may include a chronological representation of at least one of the first set of imaging data, the second set of imaging data, the first severity score, or the second severity score. In some embodiments, the method further includes spatially correlating the first and second sets of imaging data to the plurality of zones by the processor circuit. The visual representation of the plurality of zones may include selectable representations of the plurality of zones such that selection of a zone by a user displays the first and second sets of imaging data correlated to the selected zone.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
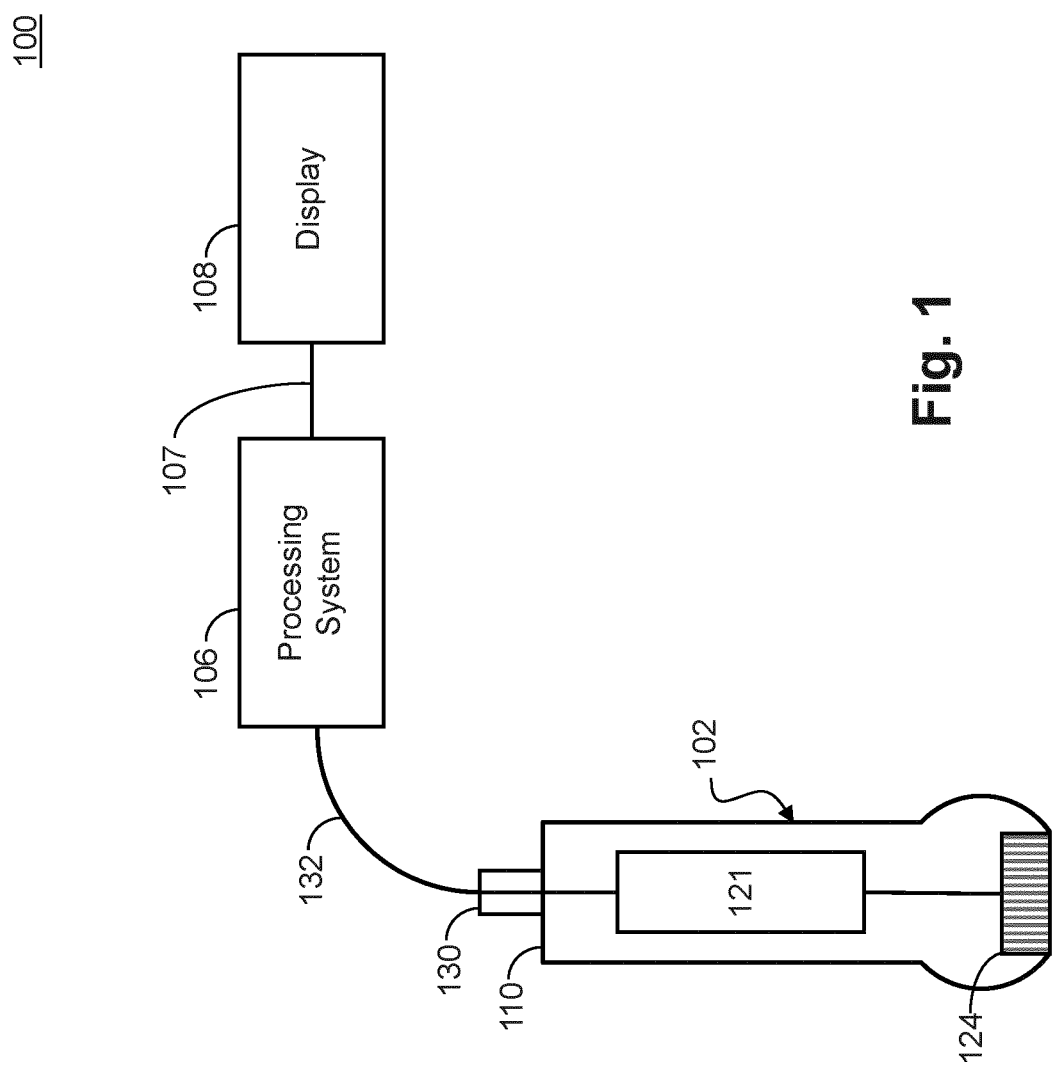
FIG. 1 is a schematic diagram of an ultrasound imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 may include an imaging device 102, a processing system 106, and a display 108. The imaging system 100 may be used to provide non-invasive imaging of body anatomy. This imaging may include 2 D or 3D B-mode ultrasonography and color flow maps. For example, the imaging device 102 may be an ultrasound probe configured to visualize anatomy inside the patient's body, while the probe is positioned outside of the patient's body. In some embodiments, the ultrasound imaging system 100 is a Doppler ultrasound imaging system. In some circumstances, the system 100 may include additional elements and/or may be implemented without one or more of the elements illustrated in FIG. 1.

The ultrasound imaging system 100 may be used in situations of blunt chest trauma, pulmonary edema, heart failure, lung failure, and other medical conditions. The system 100 may be used in pre-hospital settings, initial evaluation in the emergency room, and follow-up treatments. The system 100 is applicable to all ultrasound systems, including point-of-care application including mobile platforms. The system 100 may also be used at home by patients with remote guidance who have been discharged from a hospital, such as after lung treatment or heart failure treatment.

In some embodiments, the imaging device 102 is sized and shaped, structurally arranged, and/or otherwise configured to be placed on or near the anatomy of the subject to perform an ultrasound imaging procedure. The imaging device 102 may be positioned outside the body of a patient. In some embodiments, the device 102 is positioned proximate to and/or in contact with the body of the patient. For example, the imaging device 102 may be placed directly on the body of the subject and/or adjacent the body of the subject. For example, the imaging device 102 may be directly in contact with the body of the subject while obtaining imaging data. In some embodiments, the device 102 includes one or more imaging elements which may be placed directly on or adjacent the body of the subject. In other embodiments, a housing of the imaging device is placed directly in contact with the body of the subject such that the imaging elements are adjacent the body of the subject. The operator of the imaging device 102 may contact a distal portion of the imaging device to the body of the patient such that the anatomy is compressed in a resilient manner. The view of the anatomy shown in the ultrasound image depends on the position and orientation of the imaging device 102. To obtain imaging data of the anatomy, the imaging device 102 can be suitably positioned either manually by a clinician and/or automatically by the operator so that a transducer 124 emits ultrasound waves and receives ultrasound echoes from the appropriate portion of the anatomy. The subject may be a human patient or animal. The imaging device 102 may be portable and may be suitable to be used by a user in a medical setting. For example, the imaging device 102 may be a Doppler ultrasound imaging probe.

The imaging device 102 is configured to obtain ultrasound imaging data associated with any suitable anatomy of the patient. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, as an artery or a vein of a patient's vascular system, including cardiac vasculature, peripheral vasculature, neural vasculature, renal vasculature, and/or or any other suitable lumen inside the body. In addition to natural structures, the imaging device 102 may be used to examine man-made structures such as, but without limitation, heart valves, stents, shunts, filters and other devices.

The imaging device 102 may include a housing or handle 110 structurally arranged, sized and shaped, and/or otherwise configured for handheld grasping by a user. The handle 110 may be configured to surround and protect the various components of the imaging device 102, such as electronic circuitry 121 and the transducer array 124. The handle 110 may include internal structures, such as a space frame for securing the various components. For example, the transducer array 124 may be positioned at a distal portion of the handle 110.

The transducer elements of the array 124 may be configured to emit ultrasound signals and receive ultrasound echo signals corresponding to the emitted ultrasound signals. The ultrasound echo signals may be processed by the electronic circuitry 121 in the imaging device 102 and/or the processing system 106. The transducer array 124 can be part of an imaging assembly, including an acoustic lens and a matching material on a transmitting side of the transducer array 124, and an acoustic backing material on a backside of the transducer array 124. The transducer array 124 may include any number of transducer elements. For example, the array can include between 1 acoustic element and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5 D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy. The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The ultrasound transducer elements of the transducer array 124 are in communication with (e.g., electrically coupled to) electronic circuitry 121. The electronic circuitry 121 can be any suitable passive or active electronic components, including integrated circuits (ICs), for controlling the transducer array 124 to obtain ultrasound imaging data. For example, the electronic circuitry can include one or more transducer control logic dies. The electronic circuitry can include one or more Application Specific Integrated Circuits (ASICs) or Field Programmable Gate Array (FPGA). In some embodiments, one or more of the ICs can comprise a microbeamformer ($\mu$BF). In other embodiments, one or more of the ICs comprises a multiplexer circuit (MUX). In some instances, the electronic circuitry 121 can include a processor, a memory, a gyroscope, and/or an accelerometer.

In some embodiments, the imaging device 102 comprises an intraluminal device sized and shaped, structurally arranged, and/or otherwise configured to be positioned within a body lumen of a patient. For example, the imaging device 102 can be a guidewire, catheter, or guide catheter. In some instances, the imaging device 102 can include a gastroscope. The imaging device 102 may include a flexible elongate member, with a distal portion that is positioned within the body lumen and proximal portion that is positioned outside of the patient's body. The transducer array 124 can be coupled to the distal portion of the flexible elongate member such that the ultrasound data is obtained while positioned inside the body lumen. For example, the imaging device 102 can be an intravascular ultrasound (IVUS) catheter, an intracardiac echocardiography (ICE) catheter, and/or a transesophageal echocardiography (TEE) probe.

The processing system 106 is configured to perform one or more processing steps to generate an ultrasound image and output the ultrasound image for display by the display 108. One or more image processing steps completed by processing system 106 and/or a processor of the imaging device 102. The processing system 106 and/or the imaging device 102 can include one or more processor circuits arranged, operable, and/or otherwise configured to perform operations described herein.

Figure 2:
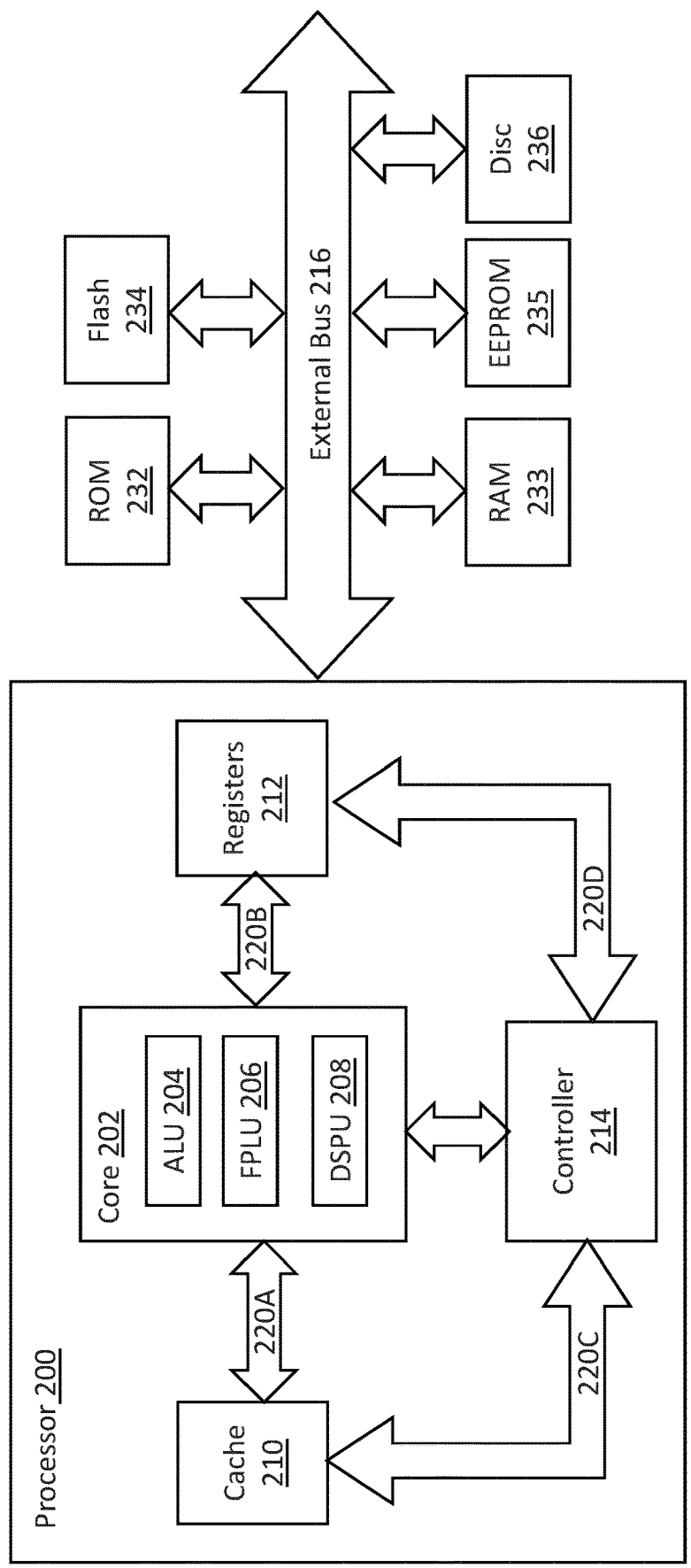
FIG. 2 is a schematic diagram of a processor circuit, according to embodiments of the present disclosure.

FIG. 2 is a block diagram illustrating an example processor 200 according to embodiments of the disclosure. Processor 200 may be used to implement one or more processors described herein, for example, the electronic circuitry 121 of the imaging device 102 and/or electronic circuitry of the processing system 106 shown in FIG. 1. The processor 200 may be used to carry out all or a portion of the processor steps described herein with respect to FIGS. 3-6. Processor 200 may be any suitable processor type including, but not limited to, a microprocessor, a microcontroller, a Digital Signal Processor (DSP), a Field Programmable Gate Array (FPGA) where the FPGA has been programmed to form a processor, a Graphical Processing Unit (GPU), an Application Specific Integrated Circuit (ASIC) where the ASIC has been designed to form a processor, or a portion of custom integrated circuit or a combination thereof. The functionality of one or more of the processors described herein, including processor 200, may be incorporated into a fewer number or a single processing unit (e.g., a CPU), which may be programmed responsive to executable instruction to perform the functions described herein. In particular, the functionality of the one or more processors may be provided by a non-transitory computer-readable medium comprising executable instructions, which when executed cause a processor circuit of an ultrasound imaging system to perform the method(s) as described herein.

The processor 200 may include one or more cores 202 (one shown). The core 202 may include one or more arithmetic logic units (ALU) 204 (one shown). In some embodiments, the core 202 may include one or more Floating Point Logic Unit (FPLU) 206 (one shown) and/or one or more Digital Signal Processing Unit (DSPU) 208 (one shown) in addition to or instead of the one or more ALU 204.

The processor 200 may include one or more registers 212 communicatively coupled to the core 202. The registers 212 may be implemented using dedicated logic gate circuits (e.g., flip-flops) and/or any suitable memory technology. In some embodiments the registers 212 may be implemented using static memory. The register may provide data, instructions and addresses to the core 202.

In some embodiments, processor 200 may include one or more levels of cache memory 210 communicatively coupled to the core 202. The cache memory 210 may provide computer-readable instructions to the core 202 for execution. The cache memory 210 may provide data for processing by the core 202. In some embodiments, the computer-readable instructions may be provided to the cache memory 210 by a local memory, for example, local memory attached to the external bus 216. The cache memory 210 may be implemented with any suitable cache memory type, for example, Metal-Oxide Semiconductor (MOS) memory such as Static Random Access Memory (SRAM), Dynamic Random Access Memory (DRAM), and/or any other suitable memory technology.

The processor 200 may include a controller 214, which may control input to the processor 200 from other processors and/or components included in the system 100 (FIG. 1) and/or outputs from the processor 200 to other processors and/or components included in the system 100. Controller 214 may control the data paths in the ALU 204, FPLU 206 and/or DSPU 208. Controller 214 may be implemented as one or more state machines, data paths and/or dedicated control logic. The gates of controller 214 may be implemented as standalone gates, FPGA, ASIC or any other suitable technology.

The registers 212 and the cache 210 may communicate with controller 214 and core 202 via internal connections 220A, 220B, 220C and 220D. Internal connections may be implemented as a bus, multiplexor, crossbar switch, and/or any other suitable connection technology.

Inputs and outputs for the processor 200 may be provided via a bus 216, which may include one or more conductive lines. The bus 216 may be communicatively coupled to one or more components of processor 200, for example the controller 214, cache 210, and/or register 212. The bus 216 may be coupled to one or more components of the system, such as electronic circuitry 121, device 102, processing system 106, and/or display 108. Bus 216 may be implemented as a bus, multiplexor, crossbar switch, and/or any other suitable connection technology The bus 216 may be coupled to one or more external memories. The external memories may include Read Only Memory (ROM) 232. ROM 232 may be a masked ROM, Electronically Programmable Read Only Memory (EPROM) 235 or any other suitable technology. The external memory may include Random Access Memory (RAM) 233. RAM 233 may be a static RAM, battery backed up static RAM, DRAM, SRAM or any other suitable technology. The external memory may include Electrically Erasable Programmable Read Only Memory (EEPROM) 235. The external memory may include Flash memory 234. The External memory may include a magnetic storage device such as disc 236. In some embodiments, the external memories may be included in a system, such as system 100 and/or processing system 106 shown in FIG. 1

Referring again to FIG. 1, the system 100 may be deployed in a medical setting, such as procedure room, catherization laboratory, operating room, emergency room, etc. The device 102 can be deployed adjacent to or in contact with the patient. The processing system 106 may be located near to the patient, e.g., in the same room as the patient. The processing system 106 can be remote from the patient, such as in a different room or different building. In some embodiments, imaging data from the device 102 is uploaded to the cloud, where it may be downloaded and processed at a remote location. The medical setting may be used to perform any number of medical imaging procedures such as Doppler ultrasound imaging, angiography, fluoroscopy, computed tomography (CT), magnetic resonance imaging (MM), intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), intracardiac echocardiography (ICE), forward-looking ICE (FLICE), intravascular palpography, transesophageal ultrasound (TEE), and other medical imaging modalities, or combinations thereof.

The imaging device 102 and display 108 may be communicatively coupled directly or indirectly to the processing system 106. For example, the imaging device 102 may be connected to the processing system 106 via connection 132, and the display 108 may be connected to the processing system via connection 107. The connections 107 and 132 can be the same type of connection or different types. Connections 107 and 132 may include a wired connection such as a standard copper link or a fiber optic link. For example, any suitable communication lines, such as conductors and/or optical fibers, can allow for data transmission between the processing system 106 and the imaging device 102 and/or the display 108. In some embodiments, the connections 107 and 132 can be a cable. In such embodiments, a connector 130 at a distal portion of the connection cable 132 can be coupled to a proximal portion of the handle 110 of the imaging device 102. The connections 107 and 132 can include any suitable communication standard, such as Ethernet, Universal Serial Bus (USB), and/or a proprietary communication protocol. In some embodiments, the connections 107 and 132 can be wireless connections using IEEE 802.11 Wi-Fi standards, Ultra Wide-Band (UWB) standards, wireless FireWire, wireless USB, or another high-speed wireless networking standard. In such embodiments, the imaging device 102, the processing system 106, and/or the display 108 may include one or more wireless transmission devices such as an antenna. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection. It should be understood that a connector such as connector 130 enables the use of one or more different imaging devices 102, such as different ultrasound transducer arrays, with processing system 106 when separate imaging procedures are conducted over time. For example, a second imaging procedure may be conducted with the same or a different ultrasound transducer arrays than was used in a first imaging procedure.

The imaging system 100 may be used to provide non-invasive imaging of anatomy, such as the heart or lungs of a patient. For example, the imaging device 102 may be configured to emit ultrasonic energy in order to create an image of a vessel or lumen and/or surrounding anatomy within the body of a patient. Ultrasonic waves emitted by a transducer array 124 of the device 102 may be reflected off tissue structures and other features within the anatomy. Echoes from the reflected waves are received by the imaging device 102 and passed along to the processing system 106. The processing system 106 processes the received ultrasound echoes to produce an image of the anatomy of the patient based on the acoustic impedance associated with the ultrasound echoes. The image may be a two-dimensional cross-sectional image or a three-dimensional image of the vessel. The imaging device 102 and/or the processing system 106 may include features similar or identical to those found in commercially available ultrasound imaging elements, e.g., the L12-4U Lumify probe and system, EPIQ, Affiniti, and/or CX50 ultrasound systems, each available from Koninklijke Philips N.V.

The imaging device 102 may be positioned outside the body of a patient. In some embodiments, the device 102 is positioned proximate to and/or in contact with the body of the patient near a vessel or lumen. The operator of the imaging device 102 may contact a distal portion of the imaging device to the body of the patient such that the anatomy is compressed in a resilient manner. The view of the anatomy shown in the ultrasound image depends on the position and orientation of the imaging device 102 and the imaging device 102 can be suitably positioned either manually by a clinician and/or automatically by the operator so that the transducer array 124 emits ultrasound waves and receives ultrasound echoes from the desired area of the anatomy.

This imaging may include dividing imaging areas into particular zones within anatomy, such as 8-28 zones. The images for each zone may be monitored over time to provide a temporal history. In some embodiments, the imaging device 102 may be used to measure one or more imaging parameters, such as B-line number, size and severity of lesions, volume and diameter of vessels, cardiac output, heart rate, light and dark zones in the lungs, amount of collapse within a lung, lung water content, and degree of consolidation. Imaging data associated with these parameters may be received by the processing system 106 and output to the display 108 to show visual representations of the anatomy, including B-mode ultrasonography and color flow maps. The imaging procedures may include measuring parameters at multiple times, such as for every one or every two breathing cycles. In some embodiments, the parameters for each zone are displayed independently, such that a medical professional can monitor changes in the parameters for each zone over time, as shown in more detail with reference to FIG. 3. The imaging data including the parameters discussed above may be transmitted to the processing system 106 for analysis. In some embodiments, imaging data and associated measurements are transmitted to the cloud and may be accessed remotely.

Figure 3:
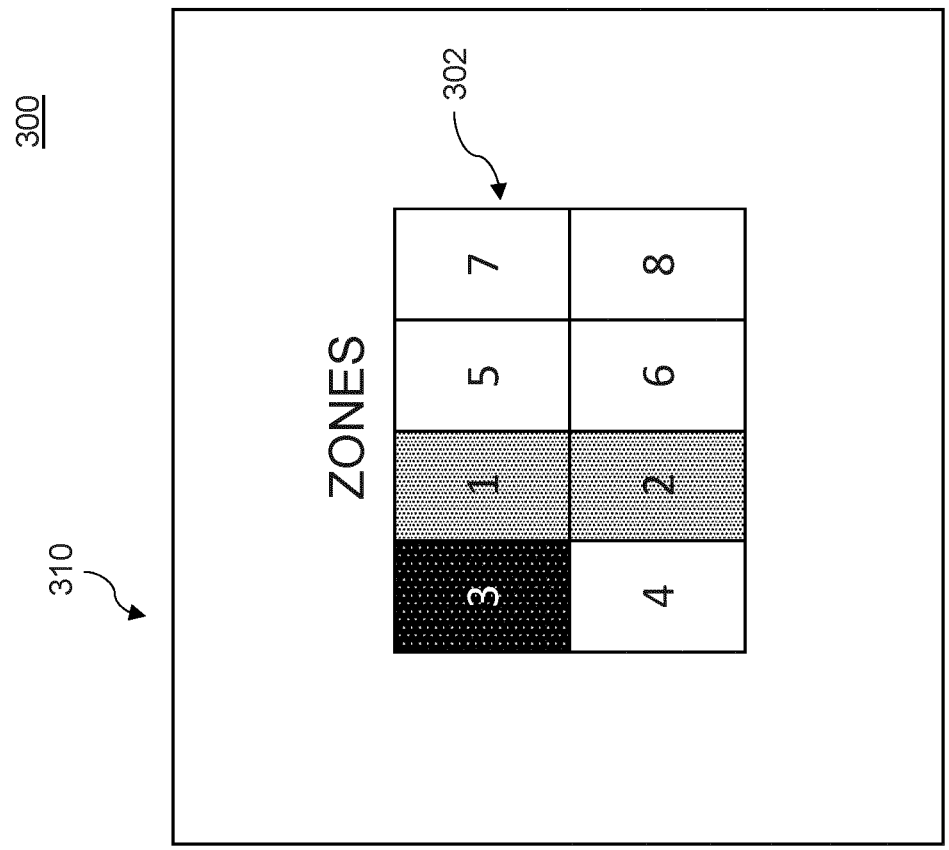
FIG. 3 is an exemplary illustration of a screen display, according to aspects of the present disclosure.
Figure 3:
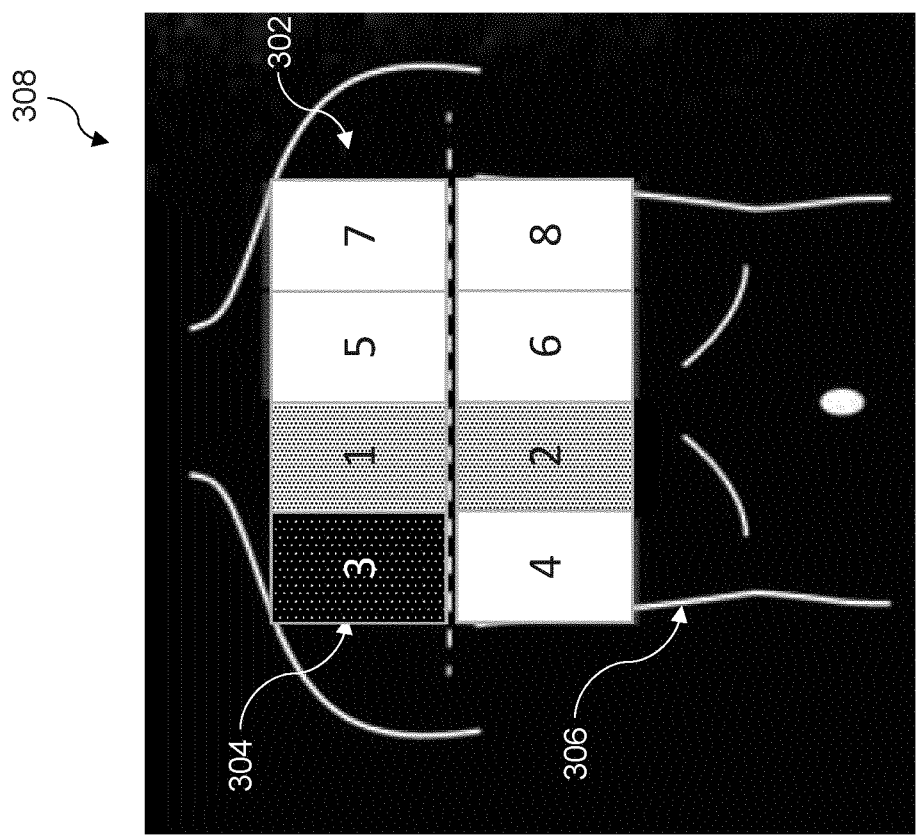

FIG. 3 shows an exemplary display 300 produced by the imaging system 100. The display may be shown on a screen of the display 108, as shown in FIG. 1. The display 300 may include windows 308, 310 showing views of the anatomy of the patient. These windows 308, 310 may include a plurality of zones 302 that may represent subdivisions of the anatomy. In the example of FIG. 3, eight zones 302 with roughly equal area are shown across the chest of a patient. Any suitable number of zones is contemplated, such as 2, 4, 6, 10, 12, 16, 20, 28, and other numbers of zones, both larger and smaller. The zones 302 may have different sizes. For example, the zones 302 may conform to a portion of the patient's anatomy e.g. a lung. The zones 302 may be based on the physiology associated with the anatomy (e.g., pulmonary edema of the lung). The size, shape, quantity, and/or location of the zones may be selected such that sufficient ultrasound data of different portions of the anatomy are obtained. The zones 302 may be selectable, such than an operator select the zone to access the imaging data associated with the zone. In some embodiments, an operator may select one or more zones via an input device (such as clicking on them with a mouse). Zones of unequal size are also contemplated and may be shown in an alternate embodiments.

In some instances, the number of zones corresponds to an ultrasound imaging protocol utilized by medical professionals to carry out ultrasound examination of the patient's anatomy. Exemplary ultrasound imaging protocols are described in Doerschug et al., *Intensive Care Ultrasound: III. Lung and Pleural Ultrasound for the Intensivist* (Annals of the American Thoracic Society, December 2013, Vol. 10, No. 6, pp. 708-712) and Volpicelli et al., *International evidence-based recommendations for point-of-care lung ultrasound* (Intensive Care Medicine, April 2012, Vol. 38, No. 4, pp. 577-591), the entireties of which are incorporated by reference herein. In some instances, a complete lung examination may include 12 zones, with 6 zones on each side of the patient's body. Each hemithorax can be divided into an anterior zone, a lateral zone, and a posterior zone, which are demarcated by the anterior axillary line and the posterior axillary line. Each of the anterior zone, the lateral zone, and the posterior zone can be divided into an upper zone and a lower/basal zone. In some instances, a lung examination includes 8 zones, omitting the two posterior zones on each side of the body described above. In some instances, a lung examination includes 2 zones. While these examples specifically mention ultrasound examination of the lungs, it is understood that the present disclosure contemplates any suitable anatomy of the patient.

The zones 302 may be colored to provide an indication of the severity of the patient's physiological condition, based on one or more imaging parameters. For example, zones 4, 5, 6, 7, and 8 are not colored, representing that they have not been imaged or have a low severity, zones 1 and 2 are colored lightly representing an acceptable severity, and zone 3 304 is darkly colored representing a high severity. The colors may be accompanied with other visual or textual cues, such as images, alerts, measurements, or messages. While colors are specifically mentioned in the description above, it is understood that the screen display 300 can include any suitable visual representation of the zones 302, including one or more shadings, patterns, textures, or images. The zones 302 may be shown with reference to the anatomy of the patient 306 (such as overlaid on a representation of the anatomy of the patient 306) in the anatomy reference window 302 as well in a standalone window 310 showing an overview of the zones 302 and accompanying information, such as measurements of the imaging parameters. The windows 308, 310 may be displayed simultaneously on the display 108. The zones 302 may be updated continuously throughout a medical procedure or across several procedures, such than a medical professional can view changes in the zones over time. This may be helpful for patients being overseen by multiple medical professionals, because a newly assigned professional can easily access the medical history for each zone 302 through the received imaging data.

Figure 4:
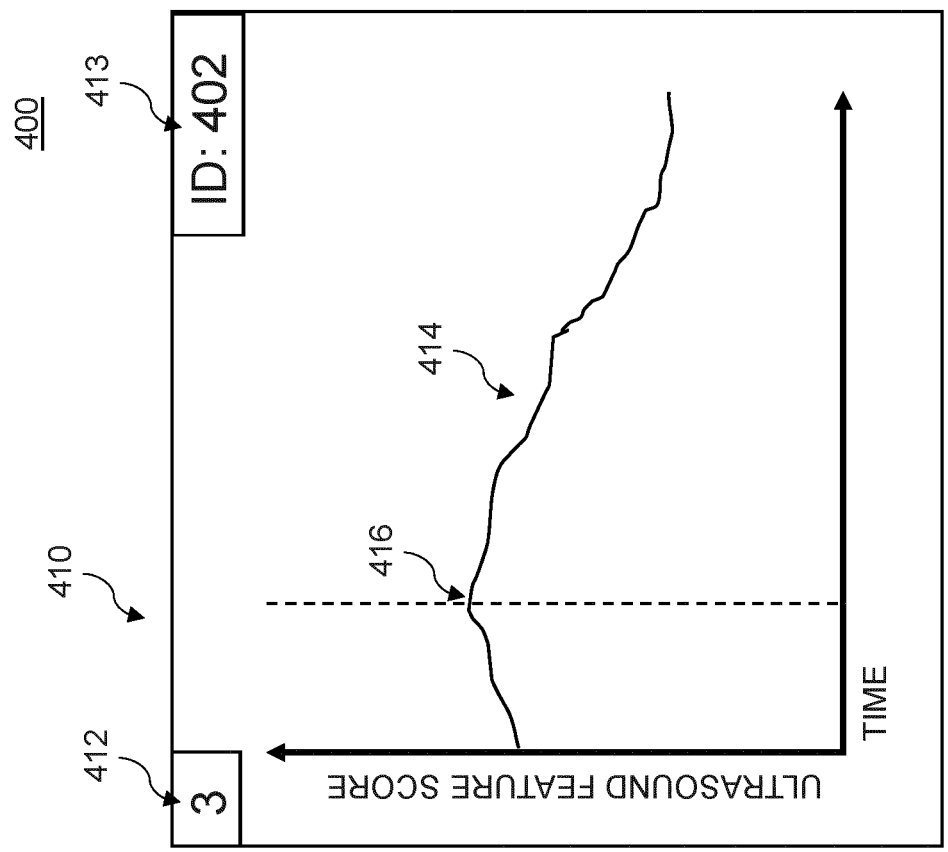
FIG. 4 is an exemplary illustration of another screen display, according to aspects of the present disclosure.
Figure 4:
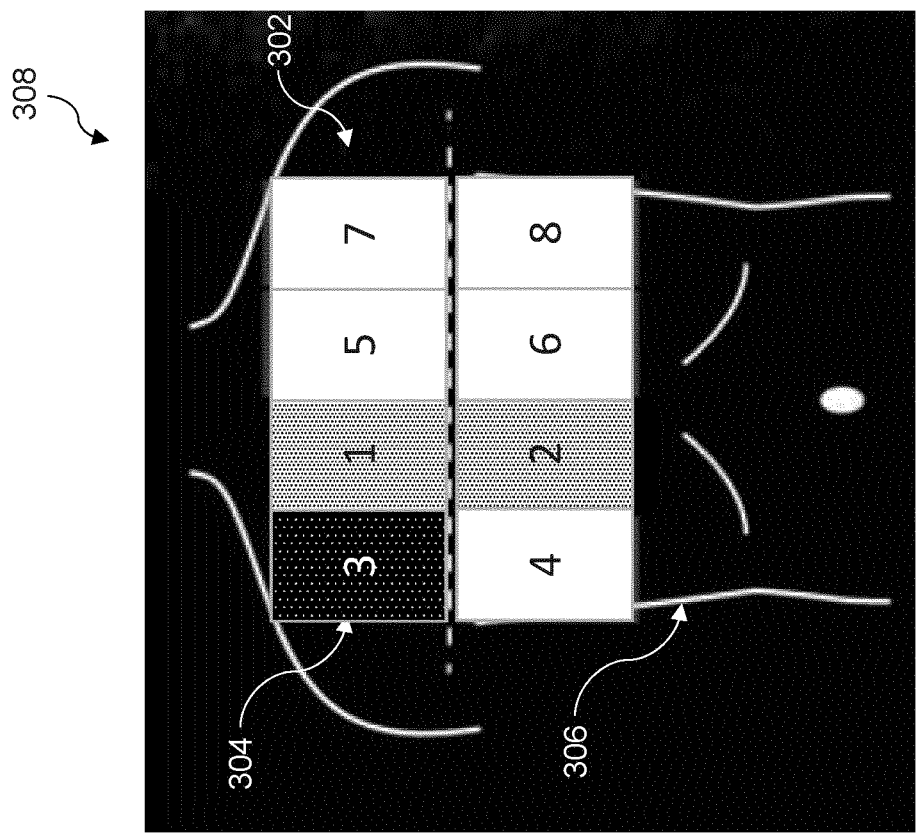

FIG. 4 shows an exemplary display 400 of the imaging system 100 which may also be shown on the display 108, as shown in FIG. 1. The display 400 may include an anatomy reference window 308 and a zone detail window 410 showing imaging information associated with a selected window. In some embodiments, a patient ID 413 is associated with all medical procedures for a particular patient. This patient ID 413 may be displayed on the display 400 and may be used to look up all medical data associated with the patient. In some embodiments, when the patient associated with the patient ID 413 is scanned by the ultrasound imaging system 100, the system 100 may automatically display the location of the zone 302 having the highest ultrasound feature score or severity score(s) in the last examination (e.g., zone 3 304).

In the example of FIG. 4, the zone detail window 410 shows severity scores over time, which are calculated by the processing system 106 based on the received ultrasound imaging data from the imaging device 102. The severity scores for a particular zone (e.g., zone 3 in the example of FIG. 4, as shown by label 412) over time may be represented by a plot, chart, or graph 314. In some embodiments, the plot 314 of the severity scores over time may be based one or more of imaging parameters of the received imaging data that are indicative of the severity of physiological condition of the patient. Generally, the severity score is a numerical quantification of the imaging parameters. Evaluation of the severity scores over time may provide an indication of whether the patient's condition is improving, worsening, or staying the same. For example, the imaging parameters can include B-line number, size and severity of lesions, volume and diameter of vessels, cardiac output, heart rate, light and dark zones in the lungs, amount of collapse within a lung, lung water content, and degree of consolidation. The plot 414 of the severity scores may include one or more reference positions 416 identifying the timing of previous treatments. The reference position 416 may represent medical procedures, administration of medication, or intervention and may be represented by a symbol, shape, point, line, color, or other visual representation. In the example of FIG. 4, the plot 414 of the severity scores shows a degree of consolidation over time for a patient with pneumonia. The disease is shown to be increasing in the patient until the reference point 416 (represented by a dotted line), where a medication was administered to the patient. After this point, the degree of consolidation (and associated severity scores in the graph 414) can be seen to be steadily decreasing over time. A medical professional may access a zone detail window 410 corresponding to each of the zones 302 with severity scores similarly measured over time.

In some embodiments, a numerical value of a severity score at a particular time is provided on the screen display 300. In some embodiments, numerical values of multiple severity scores at different times are provided. For example, the multiple severity scores can be output in in a table. The coloring of the zone 3 304 (e.g., a visual representation of the severity) on the anatomy reference window 308 may be based on the severity score at a latest point in time, a selected point of time, or an average across time.

In some embodiments, a medical professional may be able to select an imaging parameter on the display 400. In this case, the zones 302 would display a severity score associated with that parameter (e.g., a spatial distribution of the parameter across the various zones 202). In some embodiments, a medical professional adds reference points 416 manually for each medical procedure. In other embodiments, each time the patient ID 313 (in the current example, the patient ID has the value 402) is received by the processing system for a medical procedure, a reference point 306 may be added automatically. In some embodiments, the ultrasound imaging system 100 may automatically tag the zone 302 with the highest severity score (e.g., zone 3 304 in FIG. 4) such that the zone 302 is automatically shown on the display 108 at the next procedure. This may assist a medical professional in monitor problematic areas. A medical professional can also manually select one or more zones 302 for observation, such as with a mouse or touch screen. The display 400 may also be used to monitor several zones 302 within the anatomy of the patient. In this case, the temporal history for each zone 302 is automatically stored by the processing system 106 and is readily available at the next procedure. In some embodiments, the ultrasound features score for each zone may be based on at least one imaging parameter in common. In other embodiments, the ultrasound features score for two different zones may be based on different imaging parameters.

In some embodiments, the system 100 may generate suggested locations for further imaging procedures based on the results of the imaging analysis. For example, the processing system 106 may determine that zone 3 has a maximum severity score or a severity score above a chosen threshold. The threshold may be selected by the operator or fixed according to medical provider policy. The display 108 may then include a prompt to place a probe of the imaging device 102 in zone 3 to conduct a further imaging procedure.

Figure 5:
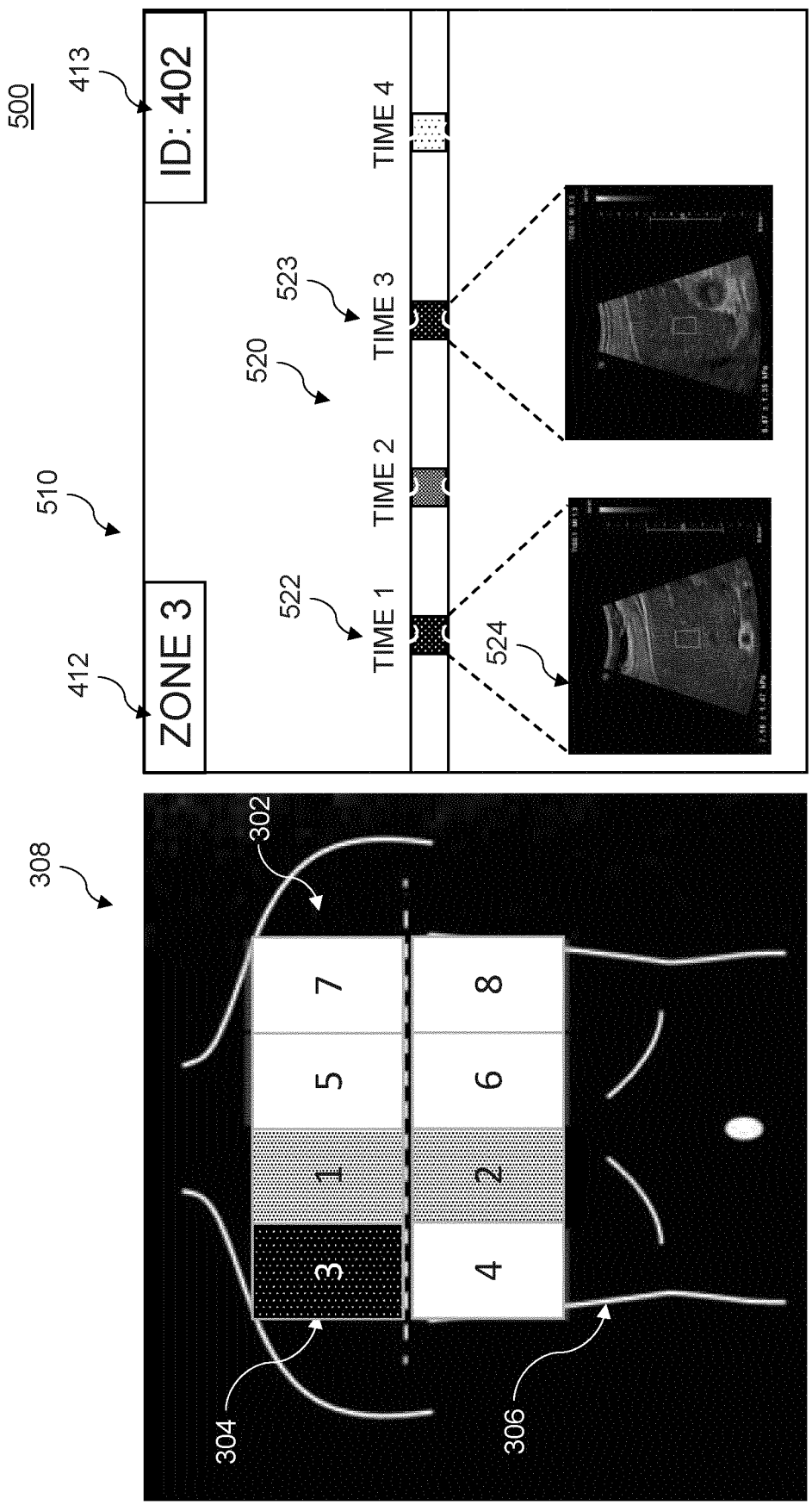
FIG. 5 is an exemplary illustration of another screen display, according to aspects of the present disclosure.

FIG. 5 shows an exemplary display 500 of the imaging system 100 which may also be shown on the display 108, as shown in FIG. 1. The display 500 may show various temporal representations of one or more zones 302. In particular, the display be used to highlight scan locations that have had high severity scores in past scans. For example, a medical professional may select zone 3 304 on the anatomy reference window 308 which may display a temporal history window 510 on the display 108 associated with zone 3. The temporal history window 510 may include one or more visual representations of a severity score over time, such as a timeline 520. In the example of FIG. 5, the timeline 520 includes severity scores represented by various colors at time 1 (severe), time 2 (moderate), time 3 (severe), and time 4 (minimal). As discussed above, the severity scores may be represented by other visual cues, such as shading, patterns, textures, images, text, or animated features. For example, a movie may be displayed with imaging data and color coding to show changes in the imaging data over time for a particular zone. The severity scores may be accompanied by corresponding imaging data. For example, the severe ultrasound scores at times 1 and 3 (reference numbers 522, 523) may include ultrasound data corresponding to those zones. The time and date of these severity scores may also be displayed, along with treatment information and notes from previous medical professionals. In some embodiments, imaging data associated with high (i.e., "severe") severity scores may be automatically displayed on the temporal history window 510 while low severity scores are not automatically displayed. This may allow the medical professional to focus on the important areas of anatomy and reduce evaluation burden, especially in critical care situations. In other embodiments, the imaging data for each severity score may be manually selected by a medical professional.

The medical information produced by the imaging system 100 and displayed on the display device 108 may be transmitted to a central location and may be accessed remotely. For example, a medical professional may access the data via a cloud location that is off site from the hospital. In this case, the medical data shown in FIGS. 3-5 may be displayed at a remote location, such as a computer monitor.

Figure 6:
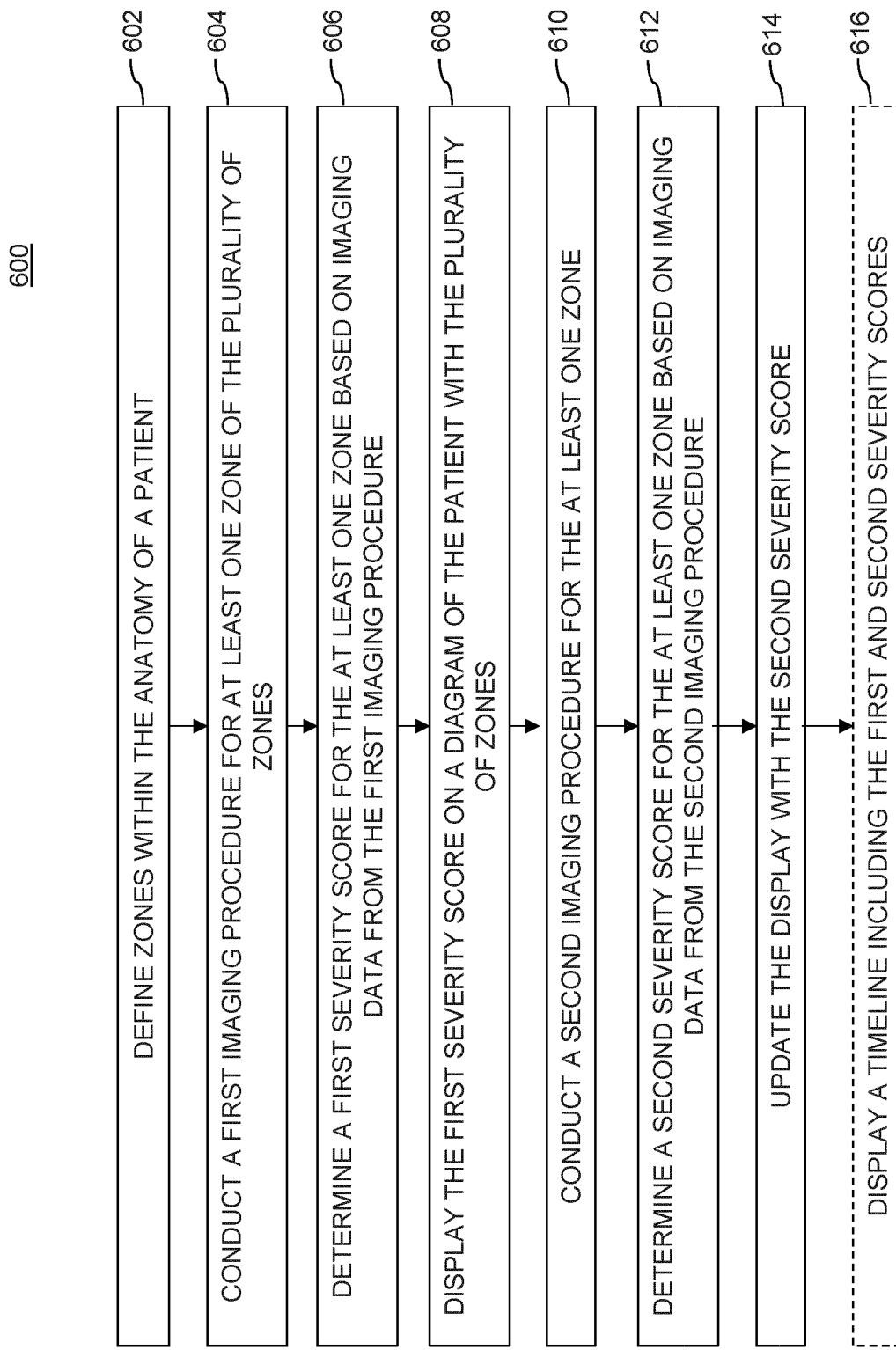
FIG. 6 is a flow chart of method of ultrasound imaging, according to aspects of the present disclosure.

FIG. 6 is a flow chart of a method 600 of ultrasound imaging. In some embodiments, the steps of the method 600 may be carried out by the ultrasound imaging system 100 and associated components as shown in FIG. 1, such as the electronic circuitry 121 of the imaging device 102, electronic circuitry of the processing system 106, and/or the display 108. For example, the processor 200 (FIG. 2) can implement all or a portion steps of the method 600. It is understood that the steps of method 600 may be performed in a different order than shown in FIG. 6, additional steps can be provided before, during, and after the steps, and/or some of the steps described can be replaced or eliminated in other embodiments.

At step 602, the method 600 may include defining a plurality of zones within the anatomy of a patient. These zones may be placed regularly across the anatomy of the patient, such as across the lungs or heart. The zones may be regular or irregular in size and shape. The number of zones may include 2, 4, 6, 10, 12, 16, 20, 28, and other numbers of zones. In some embodiments, the coordinates for each zone are also defined and stored in memory such that imaging data may be automatically spatially correlated to its zone. For example, at the start of, during, and/or at the conclusion of an imaging procedure, a user can manually indicate which zone(s) is being imaged. In some instances, the processor circuit can automatically determine, based on image processing with the obtained ultrasound data, which zone is being imaged.

At step 604, the method 600 may include conducting a first imaging procedure for at least one zone of the plurality of zones. This imaging procedure may be performed using an imaging device such as imaging device 102. The imaging procedure may include ultrasound imaging, Doppler ultrasound imaging, angiography, fluoroscopy, computed tomography (CT), magnetic resonance imaging (MRI), intravascular ultrasound (IVUS), virtual histology (VH), forward looking IVUS (FL-IVUS), intravascular photoacoustic (IVPA) imaging, optical coherence tomography (OCT), intracardiac echocardiography (ICE), forward-looking ICE (FLICE), intravascular palpography, transesophageal ultrasound (TEE), and other medical imaging modalities, or combinations thereof. In some embodiments, the imaging procedure is performed for the heart or lungs of the patient. The imaging data from the imaging procedure may be transmitted to a processing system for analysis. The imaging data may be received by a processor receiving the imaging data from the transducer array (such as during the first imaging procedure) or may be received from a processor from a memory (such as from a previously performed imaging procedure).

At step 606, the method 600 may include determining a first severity score for the at least one zone based on the imaging data from the first imaging procedure. The first severity score may be determined by a processor circuit based on one or more parameters of the imaging data. For example, image processing by the processor circuit on the obtained ultrasound data can be used to determine identify and/or quantify the one or more parameters. For example, for an imaging procedure for the heart, these parameters may include a size and severity of lesions, volume and diameter of vessels, cardiac output, and heart rate. For an imaging procedure for the lungs, the parameters may include B-line number, light and dark zones in the lungs, amount of collapse within a lung, lung water content, and degree of consolidation.

At step 608, the method 600 may include displaying the first severity score on a diagram of the patient with the plurality of zones. In some embodiments, the plurality of zones may be overlaid over a diagram of the anatomy, such that a medical professional can readily understand the location and extent of each zone. The first severity score may be represented visually for each zone, such as a color, pattern, shade, texture, or image displayed on the zone. For example, a high severity score may be displayed with a darker color while a lower severity score may be displayed with a lighter color, as in the example of FIG. 3. The zones may be selected by a medical processional, for example via a touchscreen or mouse. Selecting a zone may display further information about the zone, such as previous severity scores associated with the zone. In some embodiments, selecting a zone from the diagram may display a timeline showing the temporal history of all medical data associated with the zone.

At step 610, the method 600 may include conducting a second imaging procedure for the at least one zone. The second imaging procedure may be conducted at a later time than the first imaging procedure and may be any of the types of procedures as discussed above. In some embodiments, the second imaging procedure may be conducted for different zones than the first imaging procedure. For example, the first imaging procedure may include imaging zones 1-4 while the second imaging procedure includes imaging zones 5-8. In this case, the first and second imaging procedures may be conducted at a same time or at different times. The imaging data may from the second imaging procedure may be transmitted to a processing system for analysis. It should be understood that the second imaging procedure may be conducted with the same or a different ultrasound transducer arrays than was used in the first imaging procedure.

At step 612, the method 600 may include determining a second severity score for the at least one zone based on imaging data from the second imaging procedure. The second severity score may be based on any of the parameters discussed above.

At step 614, the method 600 may include updating the display with the second severity score. This step 514 may include updating the visual representation of the severity score, such as darkening the color of the zone for a higher severity score or lightening the color of the zone for a lower severity score.

At step 616, the method 600 may optionally include displaying a timeline including the first and second severity scores. The timeline may include accompanying information from the first and second imaging procedures, such as time and place. The timeline may also include a graph, chart, or other visual representation showing the two severity scores as well as other severity scores if available. The steps of method 600 may enable a medical professional to view the progress of the patient in particular zones of the anatomy of the patient over time. This may help to coordinate care between doctors as well as to provide special care for trouble areas of the anatomy of a patient.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
   a processor circuit configured for communication with one or more ultrasound transducer arrays that are configured to obtain imaging data associated with an anatomy of a patient, wherein the anatomy of the patient is spatially arranged in a plurality of zones comprising a first zone and a second zone,
   wherein the processor circuit is configured to:
      receive a first set of imaging data obtained by the one or more ultrasound transducer arrays at a first time, wherein the first set of imaging data is representative of the first zone and the second zone,
      determine, for each of the first zone and the second zone, a first severity score for the first time based on the first set of imaging data, wherein the first severity score is associated with an anatomical parameter,
      receive a second set of imaging data obtained by the one or more ultrasound transducer arrays at a second time, wherein the second set of imaging data is representative of the first zone and the second zone,
      determine, for each of the first zone and the second zone, a second severity score for the second time based on the second set of imaging data, wherein the second severity score is associated with the anatomical parameter,
      automatically select one of the first zone or the second zone as a selected zone, wherein the selected zone comprises:
         the first zone when the second severity score of the first zone is higher than the second severity score of the second zone; and
         the second zone when the second severity score of the second zone is higher than the second severity score of the first zone;
      output, to a display device in communication with the processor circuit:
         a visual representation of the plurality of zones; and
         a temporal representation specific to the selected zone, wherein the temporal representation simultaneously comprises a first indication of the first severity score for only the selected zone and a second indication of the second severity score for only the selected zone.

2. The ultrasound imaging system of claim 1, wherein the temporal representation illustrates a change in severity score over time based on the first severity score and the second severity score.

3. The ultrasound imaging system of claim 2, wherein the temporal representation comprises a plot of the change in severity score over time.

4. The ultrasound imaging system of claim 1, wherein the temporal representation comprises a chronological representation of the first set of imaging data and the first severity score at the first time and the second set of imaging data and the second severity score at the second time.

5. The ultrasound imaging system of claim 1, wherein the processor circuit is further configured to spatially correlate the first and second sets of imaging data to the plurality of zones.

6. The ultrasound imaging system of claim 1, wherein the visual representation of the plurality of zones comprises selectable representations of the plurality of zones such that selection of a zone by a user updates the temporal representation to display the first and second sets of imaging data correlated to the user selected zone.

7. The ultrasound imaging system of claim 1, wherein the one or more ultrasound arrays is configured to obtain imaging data associated with a lung of the patient.

8. The ultrasound imaging system of claim 7, wherein the parameter comprises at least one of a degree of consolidation, a measurement of fluid in the lungs, a degree of lung collapse, a B-line number, a measurement of air bronchogram, or a measurement of plural effusion.

9. The ultrasound imaging system of claim 1, wherein the one or more ultrasound arrays is configured to obtain imaging data associated with the heart of the patient.

10. The ultrasound imaging system of claim 9, wherein the parameter is one or more of a physical dimension of heart chamber, an ejection fraction, a degree of blockage of a blood vessel, or a volume measurement.

11. A method of conducting ultrasound imaging, comprising:
    receiving, with a processor circuit, a first set of imaging data representative of a first zone and a second zone of a plurality of zones at a first time,
       wherein the processor circuit is configured for communication with an ultrasound transducer array,
       wherein the ultrasound transducer array is arranged to obtain imaging data associated with an anatomy of a patient spatially arranged in the plurality of zones;
    determining, with the processor circuit, for each of the first zone and the second zone, a first severity score for the first time and associated with an anatomical parameter based on the first set of imaging data;
    receiving, with the processor circuit, a second set of imaging data representative of the the first zone and the second zone of the plurality of zones at a second time;
    determining, with the processor circuit, for each of the first zone and the second zone, a second severity score for the second time and associated with the anatomical parameter based on the second set of imaging data;
    automatically selecting one of the first zone or the second zone as a selected zone, wherein the selected zone comprises:
       the first zone when the second severity score of the first zone is higher than the second severity score of the second zone; and
       the second zone when the second severity score of the second zone is higher than the second severity score of the first zone; and
    outputting, to a display device in communication with the processor circuit:
       a visual representation of the plurality of zones; and a temporal representation specific to the selected zone, wherein the temporal representation simultaneously comprises a first indication of the first severity score for only the selected zone and a second indication of the second severity score for only the selected zone.

12. The method of claim 11, wherein the temporal representation illustrates a change in severity score over time based on the first severity score and the second severity score.

13. The method of claim 11, wherein the temporal representation comprises a plot of the change in severity score over time.

14. The method of claim 11, wherein the temporal representation comprises a chronological representation of the first set of imaging data and the first severity score at the first time and the second set of imaging data and the second severity score at the second time.

15. The method of claim 11, further comprising spatially correlating the first and second sets of imaging data to the plurality of zones using the processor circuit.

16. The method of claim 11, wherein the visual representation of the plurality of zones comprises selectable representations of the plurality of zones such that selection of a zone by a user updates the temporal representation to display the first and second sets of imaging data correlated to the user selected zone.

17. A non-transitory computer-readable medium comprising executable instructions, which when executed cause a processor circuit of an ultrasound imaging system to perform a method of claim 11.

* * * * *